United States Patent
McCarthy et al.

(10) Patent No.: US 7,931,591 B2
(45) Date of Patent: Apr. 26, 2011

(54) SURGICAL RETRACTOR

(76) Inventors: Patrick M. McCarthy, Chicago, IL (US); Albert N. Santilli, Pepper Pike, OH (US)

( * ) Notice: Subject to any disclaimer, the term of this patent is extended or adjusted under 35 U.S.C. 154(b) by 102 days.

(21) Appl. No.: 11/162,256

(22) Filed: Sep. 2, 2005

(65) Prior Publication Data
US 2006/0052671 A1    Mar. 9, 2006

Related U.S. Application Data

(60) Provisional application No. 60/607,475, filed on Sep. 3, 2004.

(51) Int. Cl.
*A61B 1/32*    (2006.01)
(52) U.S. Cl. .................................................. 600/232
(58) Field of Classification Search .................. 600/209, 600/211, 229, 231–234, 201, 213–215, 217, 600/221–222; 403/104, 395
See application file for complete search history.

(56) References Cited

U.S. PATENT DOCUMENTS

| | | | | |
|---|---|---|---|---|
| 3,574,364 | A | * | 4/1971 | Langren .................... 403/395 |
| 4,726,356 | A | * | 2/1988 | Santilli et al. ................ 600/232 |
| 4,852,552 | A | * | 8/1989 | Chaux ....................... 600/232 |
| 4,919,118 | A | * | 4/1990 | Morris ....................... 602/16 |
| 4,998,841 | A | * | 3/1991 | Wilde ........................ 403/104 |
| RE34,150 | E | | 12/1992 | Santilli et al. |
| 6,099,468 | A | | 8/2000 | Santilli et al. |

FOREIGN PATENT DOCUMENTS
WO    WO 2004/010859    2/2004

* cited by examiner

*Primary Examiner* — Cris L Rodriguez
*Assistant Examiner* — Hao D Mai
(74) *Attorney, Agent, or Firm* — Wayne D. Porter, Jr.

(57) ABSTRACT

A surgical retractor includes a pair of parallel arms that are mounted to a toothed crossbar. One of the arms is fixed to one end of the crossbar, while the other arm is movable along the crossbar by means of a pinion. One or both of the arms includes on its upper surface a bar having a longitudinally extending flat surface. A rod is connected to the bar by means of a bracket. The bracket can be locked in position relative to the bar by a first set screw that engages the flat surface. A rod extends through an opening in the bracket and is retained in place there by a second set screw. The rod includes a circumferentially extending shoulder that engages the bracket so as to locate the rod in a desired position. One or more flat surfaces are formed on the rod adjacent the shoulder for engagement by the second set screw. One of the flat surfaces causes the rod to be positioned precisely as necessary to perform a surgical procedure, while the other of the flat surfaces enables the rod to be moved to an out-of-the way position and locked in place there. One or more retractor blades of the wire basket type are connected to the rod by means of universal clamps. The basket portions of the retractor blades are made of a malleable wire that enables the configuration of the blades to be changed by the surgeon as desired.

17 Claims, 3 Drawing Sheets

SURGICAL RETRACTOR

CROSS-REFERENCE TO RELATED APPLICATION

This application claims priority to U.S. provisional patent application No. 60/607,475, entitled SURGICAL RETRACTOR, filed Sep. 3, 2004.

BACKGROUND OF THE INVENTION

1. Field of the Invention

The invention relates to retractors that are used in various types of surgeries such as cardiovascular surgery and, more particularly, to a retractor that can be conveniently assembled and adjusted by the surgeon.

2. Description of the Prior Art

In the course of such operative procedures as mitral valve surgery or mammary artery surgery, it is necessary to expose the heart. Such exposure has been accomplished by performing either a full or partial sternotomy (cutting an incision through the sternum and retracting the sternum) or by cutting an incision between adjacent ribs. The retraction is accomplished by a thoracic retractor that employs parallel grips that engage the edges of the incision. The grips are mounted perpendicularly to a toothed crossbar. One of the grips is fixed to one end of the crossbar, while the other grip is movably mounted to the crossbar by means of a pinion that engages the teeth of the crossbar. Upon rotating the pinion, the movable grip can be moved away from the fixed grip, thereby retracting the incision so as to expose the heart. Thoracic retractors of the type described are shown in U.S. Re. 34,150, issued Dec. 29, 1992 to A. E. Santilli and D. M. Cosgrove III, and U.S. Pat. No. 6,099,468, issued Aug. 8, 2000 to A. N. Santilli and A. Patel, the disclosures of which are incorporated herein by reference.

After the incision has been retracted, it is necessary to retract portions of the heart in order to expose diseased or defective parts thereof. Such retraction has been accomplished by attaching a cardiovascular retractor to one or both of the grips of the thoracic retractor. The cardiovascular retractor, in preferred form, includes a horizontal rod to which retractor blades having elongate handles are attached by means of universal clamps. The rod is spaced above the grip a considerable distance in order to permit the blades to have access to the heart at a favorable angle. The blades can be moved so as to engage portions of the heart to be retracted. Thereafter, upon pulling the blades and locking them in place by tightening the universal clamps, the heart can be retracted in any manner desired and maintained in that position as long as necessary.

The blades in the described construction can be moved back and forth, up and down, side to side, and they can be pivoted about the longitudinal axis of the handle. Such versatility enables the device to be used for virtually any type of cardiac surgical procedure where retraction is required. Examples of suitable cardiovascular retractors are disclosed in the '150 and the '468 patents.

While the cardiovascular retractors disclosed in the '150 and the '468 patents are effective, it takes a certain amount of effort and skill in order to assemble them properly. After assembly, certain components inadvertently can be moved into undesired positions under the forces that are placed on the retractor during the course of performing a surgical procedure. Moreover, the retractor blades themselves are fixed in shape and therefore are used on a "one size fits all" basis.

There remains a need to improve the manner in which a cardiovascular retractor is attached to a thoracic retractor. Preferably, a cardiovascular retractor could be attached to a thoracic retractor in a very simple procedure that would enable the surgeon to position the components exactly as desired without guesswork or judgment being required. Any such cardiovascular retractor hopefully would have its components retain their initial position under all operative conditions until movement to another position is desired. Moreover, the retractor blades used with the cardiovascular retractor preferably would be adjustable in order to accommodate the anatomy of different patients.

SUMMARY OF THE INVENTION

In response to the foregoing concerns, the present invention provides a new and improved surgical retractor comprising a thoracic retractor to which a cardiovascular retractor is mounted. The thoracic retractor according to the invention includes a pair of grips that are mounted to a crossbar. The grips are disposed at the ends of arms that extend from the crossbar. One of the arms is fixed to the crossbar, while the other arm is movable along the crossbar so that the grips can be moved toward or away from each other. One or both of the arms includes on its upper surface a bar that is fixed in position relative to the arm. Preferably, the arm and its associated bar have longitudinal axes that are parallel with each other.

A first rod is connected to the bar on a selected arm by means of a first bracket. Optionally, a second rod is connected to the bar on the other arm by means of a second bracket. The brackets carry first set screws that enable the brackets to be locked in position relative to their respective bars. The brackets are slidable along the bars in order to permit the longitudinal position of the rods relative to the arms to be adjusted. The brackets are large enough that the rods are disposed above the arms a desired distance. Each bar includes a longitudinally extending flat surface. The first set screw engages the flat surface so as to locate the bracket and its associated rod in a precise rotational position relative to the bar. The interaction of the first set screw and the flat surface also prevents the relative position of the components from being changed under forces that may be applied during the course of a surgical procedure.

In the preferred embodiment, the first rod is L-shaped, while the second rod is straight. Each of the rods extends through an opening in its associated bracket and is retained in place there by a second set screw. Each rod preferably includes a circumferentially extending shoulder on the part that extends through the opening in the bracket. The shoulder enables the rod to be positioned exactly as desired relative to the arm to which it is connected. Preferably a flat surface is formed on the rod adjacent the shoulder for engagement by the second set screw. The flat surface causes the rod to be positioned precisely as necessary to perform a surgical procedure. In the particular case of the L-shaped rod, a second flat surface can be provided that is spaced circumferentially from the first flat surface. The second flat surface enables the L-shaped rod to be moved to an out-of-the way position and locked in place there.

The rods enable one or more small retractor blades of the wire basket type having elongate handles to be used to retract portions of the heart. Each retractor blade is connected to one of the rods by means of a universal clamp that grasps both the handle of the blade and the rod. Each clamp includes a nut that enables the clamp to be tightened or loosened with one hand. The clamps permit the blades to be moved to any position that may be desired by the surgeon. The basket portions of the retractor blades are made of a malleable wire that enables the configuration of the blades to be changed by the surgeon as desired.

As will be appreciated from the foregoing description, the cardiovascular retractor according to the invention can be attached to the thoracic retractor according to the invention in a very simple procedure that will enable the surgeon to position the components exactly as desired without guesswork or judgment being required. The components of the cardiovascular retractor will retain their initial position under all operative conditions until movement to another position is desired. In addition, the basket portions of the retractor blades according to the invention are adjustable in order to accommodate the anatomy of different patients.

The foregoing and other features and advantages of the invention will be apparent from a review of the following description of the invention, together with the attached drawings.

DESCRIPTION OF THE PREFERRED EMBODIMENT

Figure 1:
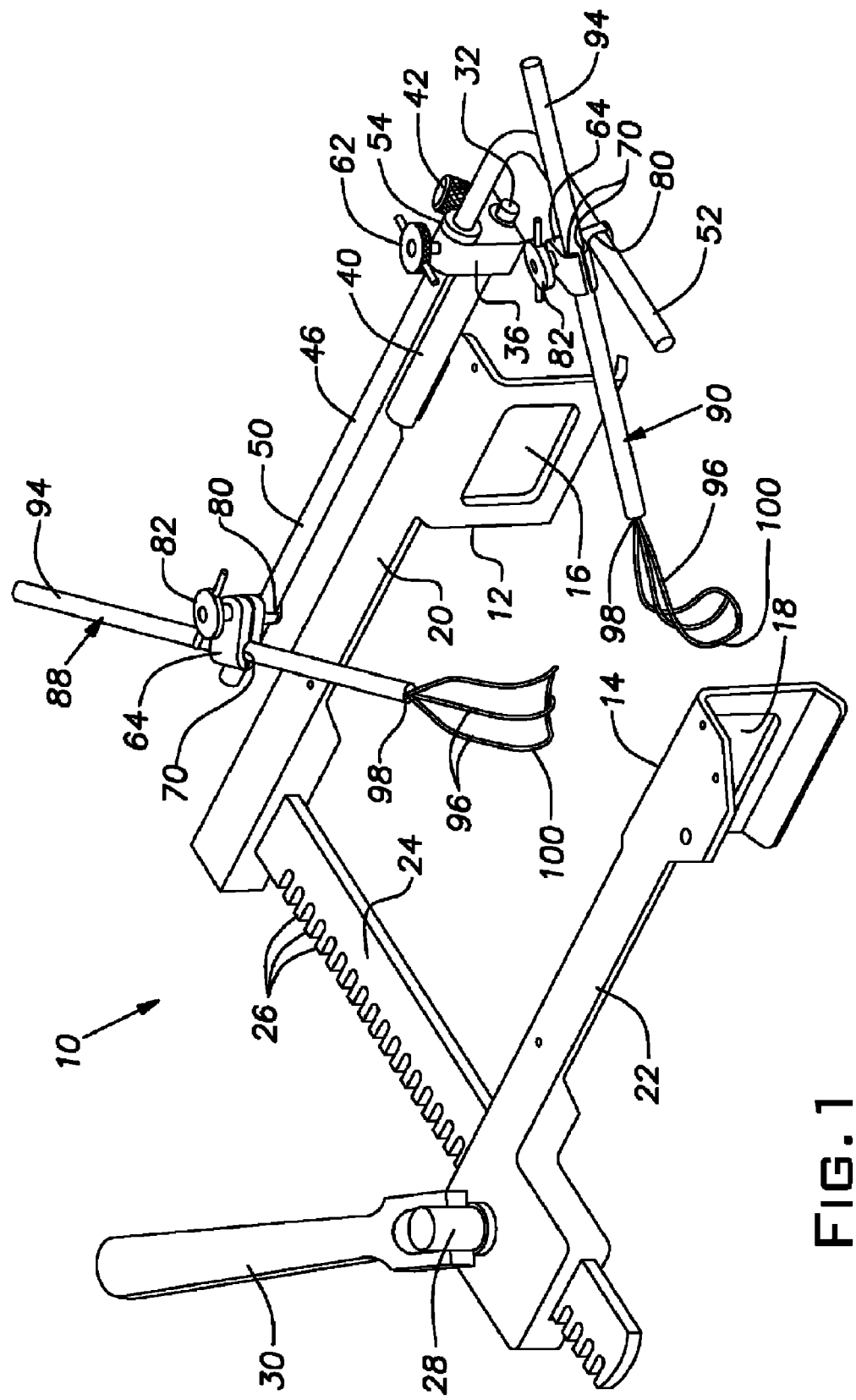
FIG. 1 is a perspective view of a surgical retractor according to the invention.

Referring generally to FIGS. 1-5, a surgical retractor according to the invention is indicated generally by the reference numeral 10. The retractor 10 includes a pair of small, generally rectangular parallel grips 12, 14. The grips 12, 14 have rectangular openings 16, 18 formed therein, respectively. The grips 12, 14 are mounted at the ends of arms 20, 22, respectively.

The arms 20, 22 extend at right angles away from a crossbar 24 having a plurality of spaced teeth 26. The arm 20 is fixed to the crossbar 24, while the arm 22 is movable along the crossbar 24 so as to move the grip 14 toward or away from the grip 12. Movement of the arm 22 is accomplished by a pinion 28 that engages the teeth 26 of the crossbar 24. A handle 30 is connected to the pinion 28 for purposes of rotating the pinion 28.

Figure 2:
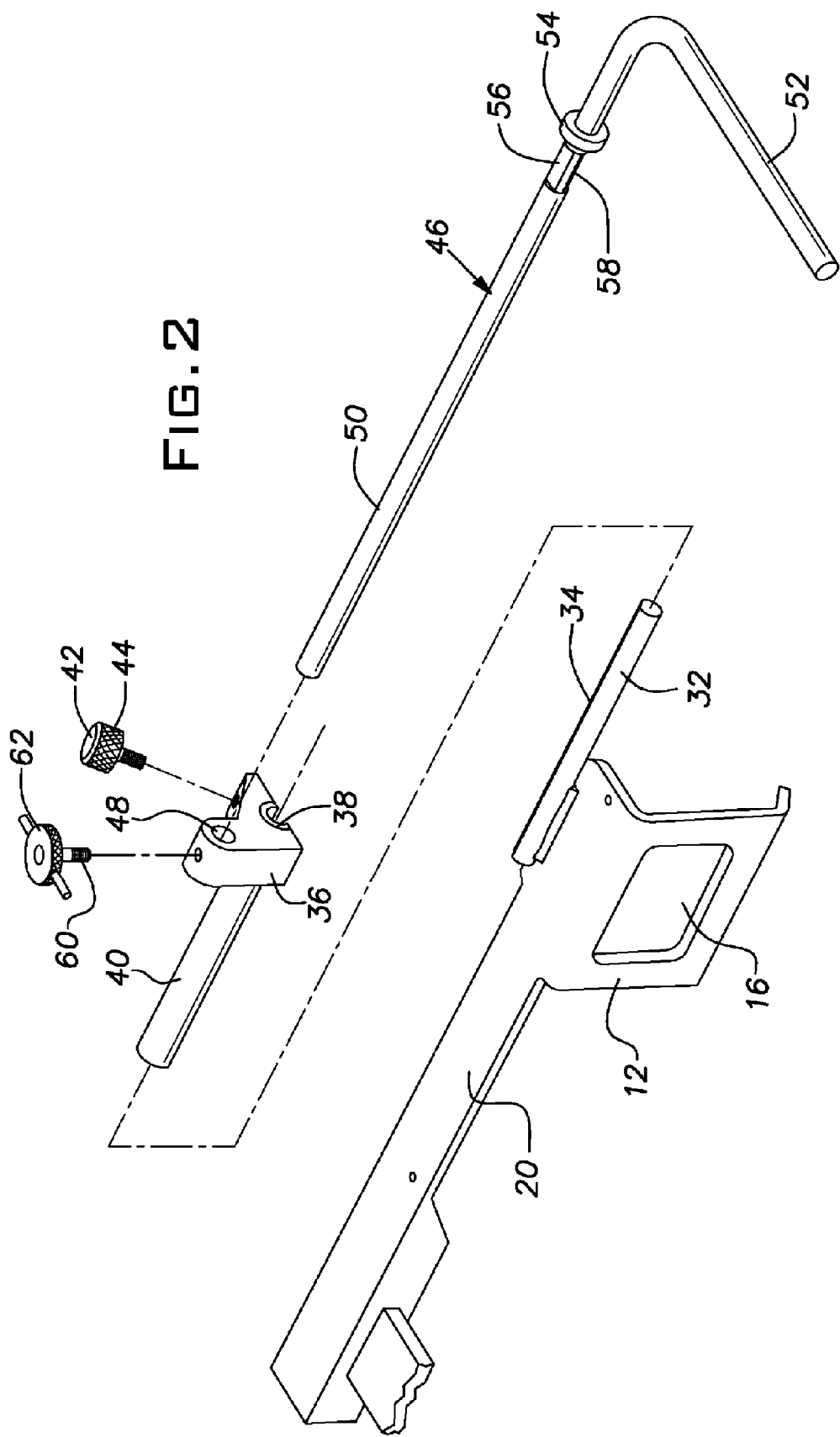
FIG. 2 is an exploded perspective view of portions of the surgical retractor of FIG. 1.

A generally cylindrical bar 32 is mounted to the upper surface of one or both of the arms 20, 22. For convenience, only one bar 32 will be discussed herein, and such discussion will be only with respect to the arm 20. The bar 32 is secured to the fixed arm 20 by any convenient technique such as riveting or welding. As can be seen in FIGS. 1 and 2, the bar 32 is disposed at the end of the arm 20. The longitudinal axis of the bar 32 is parallel or generally parallel with the longitudinal axis of the arm 20. The bar 32 has a longitudinally extending flat surface 34.

Figure 3:
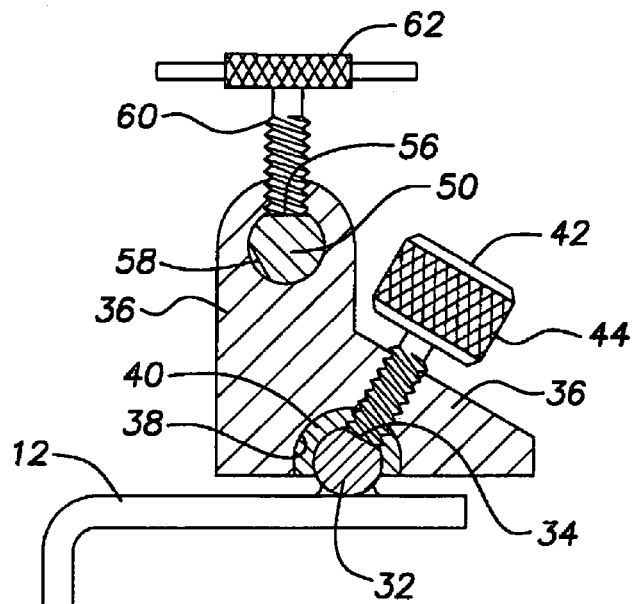
FIG. 3 is a cross-sectional view of a portion of the surgical retractor according to the invention showing a bracket disposed atop an arm and carrying a rod.

A bracket 36 is secured to the bar 32 so as to extend upwardly from the upper surface of the arm 20. Referring particularly to FIG. 3, the bracket 36 has a longitudinally extending groove 38 within which a sleeve 40 is disposed. The sleeve 40 is open on its underside. The inner diameter of the sleeve 40 is slightly larger than the outer diameter of the bar 32 so that a relatively tight fit between the two can be made.

The bracket 36 carries a first set screw 42 that has a knurled knob 44 at its outer end. The set screw 42 extends through aligned threaded openings in the bracket 36 and the sleeve 40. The bracket 36 can be moved along the bar 32 until a desired longitudinal position has been attained. Thereafter, the end of the set screw 42 can be tightened against the flat surface 34 so as to secure the bracket 36 in place. By appropriately locating the flat surface circumferentially about the longitudinal axis of the bar 32, the bracket 36 will be positioned relative to the arm 20 in an optimum position. Moreover, the interaction of the flat surface 34 and the end of the set screw 42 will prevent the bracket 36 from rotating about the longitudinal axis of the bar 32 under forces that may occur during the course of a surgical procedure.

A cylindrical rod 46 extends through an opening 48 formed in the bracket 36. The rod 46 is L-shaped, with a first section 50 that is disposed parallel to the longitudinal axis of the arm 20 and a second section 52 that is disposed perpendicular to the first section 50. The second section 52 extends toward the second arm 22. A circumferentially extending shoulder 54 is disposed on the first section 50. First and second flat surfaces 56, 58 are formed on the first section 50 immediately adjacent the shoulder 54. The flat surfaces 56, 58 are positioned about 120 degrees apart from each other.

The bracket 36 carries a second set screw 60 that has a knurled knob 62 at its outer end. The set screw 60 extends through a second threaded opening in the bracket 36. The first section 50 of the rod 46 can be moved through the opening 48 until the shoulder 54 engages the side of the bracket 36. Thereafter, the end of the set screw 60 can be tightened against the first flat surface 56 so as to secure the rod 46 in place within the bracket 36. By appropriately locating the flat surface 34 on the bar 32 and the first flat surface 56 on the rod 46, the second section 52 will be positioned relative to the arm 20 in an optimal horizontal or nearly horizontal position. Moreover, the interaction of the flat surface 56 and the end of the set screw 60 will prevent the rod 46 from rotating about the longitudinal axis of the first section 50 under forces that may occur during the course of a surgical procedure.

Figure 4:
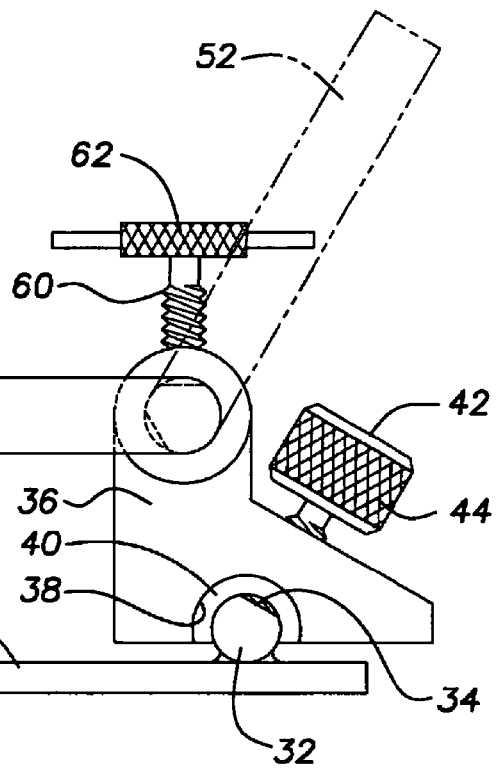
FIG. 4 is an elevation view similar to FIG. 3 showing different positions to which the rod can be moved.

Referring to FIG. 4, either before a surgical procedure has been commenced or after it has been completed, the rod 46 can be positioned so that the second section 52 is rotated about the longitudinal axis of the first section 50 up and out of the surgical field. The second section 52 can be retained in position there by tightening the end of the set screw 60 against the second flat surface 58. Since the flat surfaces 56, 58 are circumferentially spaced about 120 degrees from each other, the second section 52 will be disposed about 120 degrees from a horizontal position.

The retractor 10 includes several universal clamps 64 that are used to hold retractor blades in a variety of desired positions. Because the clamps 64 are identical, only one of them will be described herein. The clamp 64 includes a first finger 66 and a second finger 68. The fingers 66, 68 are disposed immediately adjacent each other. A groove 70 is formed in the ends of each of the fingers 66, 68 so that the grooves 70 face each other. A guide pin 72 extends between, and connects, the fingers 66, 68. Similarly, a threaded pin 74 extends through the fingers 66, 68. A sleeve 78 is disposed about the pin 74. The sleeve 78 includes a pair of opposed, U-shaped slots 80. A nut 82 is threaded onto the pin 74. A spring (not shown) is disposed between the opposed fingers 66, 68. The spring is disposed about that portion of the threaded pin 74 that extends between the fingers 66, 68.

Retractor blades 88, 90 are provided for use with the invention. Reference is made to International Publication No. WO 2004/010859 A1, published Feb. 5, 2004, the disclosure of which is incorporated herein by reference, for a disclosure of retractor blades having a configuration that would be suitable for the retractor blades 88, 90. Each of the blades 88, 90 includes an elongate, cylindrical handle 94. The handle 94 is of a size that can be grasped by the grooves 70 of the opposed fingers 66, 68. The retractor blades 88, 90 have wire basket end portions comprised of wire spokes 96 that are connected at their ends by a knurled rod 98. The spokes 96 are relatively straight and generally lie in a common plane, except for end portions that are bent back upon themselves to form a hooked portion 100. A feature of the spokes 96 is that they are made of piano wire having a very small diameter on the order of 0.0625 inch. Such material is very strong, yet malleable enough to permit the surgeon to adjust the shape of the basket end portions to suit the needs of each patient.

Figure 5:
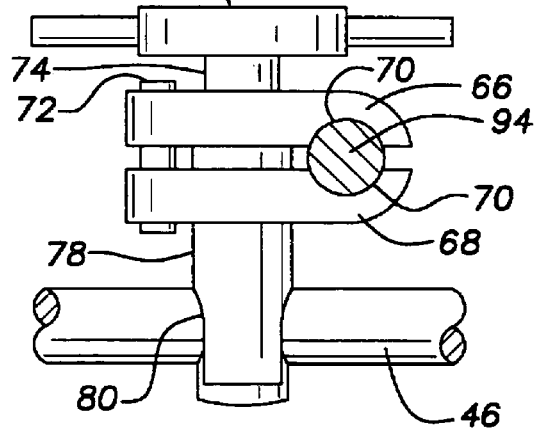
FIG. 5 is a view of a universal clamp that can be used to hold the handle of a retractor blade.

As will be apparent from an examination of FIGS. 1 and 5, the rod 46 can be fitted through the aligned bores and slots 80. The handle 94 can be fitted between the opposed grooves 70 and moved to any position desired. When it is desired to fix a selected retractor blade 88, 90 in any particular position, the nut 82 is tightened. As the nut 82 is tightened, the rod 46 will be compressed against the slots 80, thereby tightening the rod 46 in place. Continued tightening of the nut 82 will cause the fingers 66, 68 to be moved toward each other against the opposing force of the spring. Eventually, the grooves 70 will tightly engage the handle 94, thereby locking the handle 94 and the clamp 64 in place on the rod 46. By virtue of the foregoing construction, the user can use one hand to grasp the handle 94 and retract the selected retractor blade 88, 90 to any desired position. Using the other hand, the nut 82 can be tightened after the desired position of the blade 88, 90 has been attained. This is a very convenient and effective way to securely position the blades 88, 90 in a desired position.

It is expected that the retractor 10 will be used as follows. Initially, the pinion 28 will be rotated by turning the handle 30 so that the arm 22 will be moved toward the arm 20. Accordingly, the grips 12, 14 will be immediately adjacent each other. Due to the small size and shape of the grips 12, 14, the thoracic cavity need be opened only a small amount, for example, a distance of about four inches. After inserting the grips 12, 14 into the incision, the sternum or ribs can be retracted by turning the handle 30 to move the grip 14 away from the grip 12.

After the grips 12, 14 have been moved apart, the bracket 36 is attached to the bar 32 as indicated in FIGS. 1 and 2. The knob 44 is rotated to tighten the end of the set screw 42 against the flat surface 34 to lock the bracket 36 in place. Thereafter, the first section 50 is inserted into the upper opening 48 in the bracket 36 until the shoulder 54 contacts the side of the bracket 36. The knob 62 is rotated to tighten the end of the set screw 60 against a selected flat surface 56, 58. As indicated previously, if the first flat surface 56 is employed, the second end 52 of the rod 46 will be maintained in an optimal horizontal or near-horizontal position. After the rod 46 has been positioned as desired, the clamps 64 are used to position the retractor blades 88, 90 as may be necessary to adequately expose the heart or other desired portion of the patient.

As will be apparent from the foregoing description, a surgical retractor according to the invention includes a cardiovascular retractor that can be attached to a thoracic retractor in a very simple procedure that will enable the surgeon to position the components exactly as desired without guesswork or judgment being required. The components of the cardiovascular retractor will retain their initial position under all operative conditions until movement to another position is desired. In addition, the basket portions of the retractor blades according to the invention are adjustable in order to accommodate the anatomy of different patients.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A surgical retractor especially adapted for retracting portions of a patient's body by use of one or more retractor blades, comprising:
   first and second arms having first and second grips, respectively, for engaging and being maintained in position relative to selected portions of the patient;
   a crossbar that connects the first and second arms, the first arm being rigidly connected to the crossbar and the second arm being movable along the crossbar toward or away from the first arm;
   each of the first and second arms having an upper surface;
   an elongate bar secured to the upper surface of a selected one of the first or second arms, the elongate bar being fixed in position relative to the arm, the elongate bar defining a longitudinal axis and having a flat surface along at least a portion of its length;
   a bracket extending upwardly from the upper surface of the selected arm and to which one or more retractor blades can be connected, the bracket having a groove on that side facing the upper surface, the groove having a size and shape such that it can engage the elongate bar and be retained there for axial movement along the longitudinal axis and rotational movement about the longitudinal axis;
   a first threaded opening in the bracket; and
   a first set screw threaded into the first threaded opening, the first set screw being engageable with the flat surface on the elongate bar in order to prevent axial movement of the bracket and any retractor blade connected thereto along the longitudinal axis and rotational movement of the bracket and any retractor blade connected thereto about the longitudinal axis, whereby the bracket and any retractor blade connected thereto can be located in a fixed, predetermined position relative to the patient.

2. The surgical retractor of claim 1, wherein the arm to which the bracket is connected has a longitudinal axis, and further comprising:
   an opening in the bracket, the opening in the bracket being disposed above the upper surface of the arm to which the bracket is connected, the opening in the bracket having a longitudinal axis that is generally parallel with the longitudinal axis of the arm;
   a first, elongate rod for supporting one or more retractor blades, the first rod extending through the opening in the bracket and being oriented generally parallel to the longitudinal axis of the arm;
   the first rod having first and second ends and a circumferentially extending shoulder disposed between the first and second ends;
   a flat surface formed on the first rod at a location adjacent the shoulder;

a second threaded opening in the bracket, the second threaded opening extending into the opening in the bracket; and a second set screw threaded into the second threaded opening, the second set screw being engageable with the flat surface on the rod when the shoulder is in contact with the bracket in order to prevent longitudinal and rotational movement of the rod relative to the bracket.

3. The retractor of claim 2, further comprising:

at least one retractor blade having an elongate handle and a wire basket-type end portion at one end of the handle; and a universal clamp that is connected to the rod and to which the handle of the retractor blade is connected, the universal clamp being selectively movable relative to the rod and the handle being selectively movable relative to the clamp.

4. The surgical retractor of claim 1, wherein the arm to which the bracket is connected has a longitudinal axis, and further comprising:

an opening in the bracket, the opening in the bracket being disposed above the upper surface of the arm to which the bracket is connected, the opening in the bracket having a longitudinal axis that is generally parallel with the longitudinal axis of the arm;

a generally L-shaped rod for supporting one or more retractor blades, the generally L-shaped rod having first and second sections, the first section extending through the opening in the bracket and being oriented generally parallel with the longitudinal axis of the arm;

the first section having first and second ends and a circumferentially extending shoulder disposed between the first and second ends;

a first flat surface formed on the first section at a location adjacent the shoulder;

a second threaded opening in the bracket, the second threaded opening extending into the opening in the bracket; and a second set screw threaded into the second threaded opening, the second set screw being engagable with the first flat surface on the first section when the shoulder is in contact with the bracket in order to prevent longitudinal and rotational movement of the L-shaped rod relative to the bracket.

5. The surgical retractor of claim 4, wherein:

the crossbar has an upper surface that lies in a plane;

the upper surfaces of the arms define planes that are generally parallel with the upper surface of the crossbar; and the flat surface on the bar and the first flat surface are located such that the second section of the rod is generally parallel with the plane defined by the upper surface of the arm to which it is connected when the first set screw engages the flat surface on the bar and the second set screw engages the first flat surface on the rod.

6. The surgical retractor of claim 4, further comprising a second flat surface formed on the first section of the rod at a location adjacent the shoulder, the second flat surface being spaced circumferentially from the first flat surface.

7. The surgical retractor of claim 6, wherein:

the crossbar has an upper surface that lies in a plane;

the upper surfaces of the arms define planes that are generally parallel with the upper surface of the crossbar; and the flat surface on the bar and the second flat surface on the rod are located such that the second section of the rod is generally perpendicular to the plane defined by the upper surface of the arm to which it is connected when the first set screw engages the flat surface on the bar and the second set screw engages the second flat surface on the rod.

8. The surgical retractor of claim 7, wherein the first and second flat surfaces are spaced from each other approximately 120 degrees.

9. The retractor of claim 4, further comprising:

at least one retractor blade having an elongate handle and a wire basket-type end portion at one end of the handle; and a universal clamp that is connected to the rod and to which the handle of the retractor blade is connected, the universal clamp being selectively movable relative to the rod and the handle being selectively movable relative to the clamp.

10. The retractor of claim 1, further comprising an elongate, open-sided sleeve disposed within said groove, the sleeve having an outer surface that engages the groove and an inner surface that engages the bar, the open side of the sleeve and the open side of the bracket generally being aligned with each other.

11. A surgical retractor, comprising:

first and second arms having first and second grips, respectively;

a crossbar to which the first and second arms are connected, the first arm being rigidly connected to the crossbar and the second arm being movable along the crossbar toward or away from the first arm, the crossbar having an upper surface that lies in a plane;

each of the first and second arms having an upper surface that is generally parallel with the upper surface of the crossbar;

a bracket connected to and extending upwardly from the upper surface of a selected one of the first or second arms, the arm to which the bracket is connected having a longitudinal axis;

an opening in the bracket, the opening in the bracket being disposed above the upper surface of the arm to which the bracket is connected, the opening in the bracket having a longitudinal axis that is generally parallel with the longitudinal axis of the arm to which the bracket is connected;

a rod for supporting one or more retractor blades, the rod being generally L-shaped and having first and second sections, the first section extending through the opening in the bracket and oriented generally parallel with the longitudinal axis of the arm to which the bracket is connected, the rod being movable longitudinally and rotationally relative to the bracket;

the first section having first and second ends and a circumferentially extending shoulder disposed between the first and second ends;

a first flat surface formed on the first section at a location adjacent the shoulder;

a threaded opening in the bracket, the threaded opening extending into the opening in the bracket;

a set screw threaded into the threaded opening, the set screw being engageable with the first flat surface on the first section when the shoulder is in contact with the bracket in order to prevent longitudinal and rotational movement of the rod relative to the bracket; and the first flat surface is located such that the second section of the rod is generally parallel with the plane defined by the upper surface of the arm to which it is connected when the set screw engages the first flat surface.

12. The surgical retractor of claim 11, further comprising a second flat surface formed on the first section at a location adjacent the shoulder, the second flat surface being spaced circumferentially from the first flat surface.

13. The surgical retractor of claim 12, wherein:
the second flat surface is located such that the second section of the rod is generally perpendicular to the plane defined by the upper surface of the arm to which it is connected when the set screw engages the second flat surface.

14. The surgical retractor of claim 13, wherein the first and second flat surfaces are spaced from each other approximately 120 degrees.

15. The surgical retractor of claim 11, further comprising:
at least one retractor blade having an elongate handle and a wire basket-type end portion at one end of the handle; and
a universal clamp that is connected to the rod and to which the handle of the retractor blade is connected, the universal clamp being selectively movable relative to the rod and the handle being selectively movable relative to the clamp.

16. The surgical retractor of claim 11, wherein at least one retractor blade comprises an end portion defined by a plurality of generally parallel spokes that are connected at one end to an elongate handle, the improvement comprising:
the spokes being made of a malleable material such that the configuration of the end portion can be changed to suit the anatomy of each patient.

17. The retractor blade of claim 16, wherein the spokes are made of piano wire having a diameter of approximately 0.0625 inch.

* * * * *